United States Patent [19]
Iwai et al.

[11] Patent Number: 6,022,718
[45] Date of Patent: Feb. 8, 2000

[54] METHOD OF PRODUCING CAPSAICIN ANALOGUES

[75] Inventors: Kazuo Iwai, Kyoto; Tatsuo Watanabe, Shizuoka; Yukiyoshi Tamura; Susumu Ogawa, both of Hiroshima, all of Japan

[73] Assignee: Maruzen Pharmaceuticals Co., Ltd., Onomichi, Japan

[21] Appl. No.: 09/217,594

[22] Filed: Dec. 21, 1998

[30] Foreign Application Priority Data

Jul. 2, 1998 [JP] Japan ................................. 10-201078

[51] Int. Cl.$^7$ ............................. C12P 13/02; C12N 9/20
[52] U.S. Cl. ........................................... 435/129; 435/198
[58] Field of Search ..................................... 435/129, 198

[56] References Cited

PUBLICATIONS

ACS Caplus Computer Abstract 1998:427444 Kobata et al "Biotechnol. Lett." 20(5) pp. 451–454, May 1998.

ACS Caplus Computer Abstract 1998:680926 Kobata et al "Biotechnol. Lett." 20(8) pp. 781–783, Aug. 1998.

*Primary Examiner*—Herbert J. Lilling
*Attorney, Agent, or Firm*—Oblon, Spivak, McClelland, Maier & Neustadt, P.C.

[57] ABSTRACT

A method of producing a capsaicin analogue, comprising reacting a fatty acid having 12 or more carbon atoms or an ester thereof (inclusive of fats and oils) with capsaicin in the presence of lipase to produce an N-vanillyl fatty acid amide having an acyl group containing 12 or more carbon atoms, and a method of producing fats and oils containing capsaicin analogues, comprising reacting edible fats and oils with capsaicin in the presence of lipase to produce N-vanillyl fatty acid amides from a portion of the edible fats and oils are provided. It is possible to produce non-pungent capsaicin analogues and other capsaicin analogues, which facilitates utilization of non-pungent capsaicin analogues in the food industry.

16 Claims, No Drawings

METHOD OF PRODUCING CAPSAICIN ANALOGUES

BACKGROUND OF THE INVENTION

1. Field of the Invention

The present invention relates to a method of producing N-vanillyl fatty acid amides other than capsaicin, and particularly producing capsaicin analogues having a non-pungent-taste, from capsaicin, which is a component contained in red peppers that has a pungent taste.

The present invention also relates to a method of producing fats and oils containing capsaicin analogues with a non-pungent-taste.

2. Description of Related Art

The major pungent components of red peppers, which are widely used as a spice, include capsaicin (8-methyl-N-vanillyl-6-nonenamide) and dihydrocapsaicin (8-methyl-N-vanillyl-nonanamide), which are N-vanillyl fatty acid amides having 10 carbon atoms in their acyl group (hereinafter, also referred to as "capsaicins", inclusive of dihydrocapsaicin).

Capsaicins are known to not only give a strong pungent-taste but also have various effects useful to living organisms such as an appetite promoting effect, a vasodilating/ vasoconstricting effect, a salivation stimulating effect, a gastric acid secretion stimulating effect, an intestinal peristalsis stimulating effect, a circulatory cholesterol level reducing effect, an energy metabolism enhancing effect, a bioactive peptide release stimulating effect and the like.

In particular, explanation of its energy metabolism stimulating effect has recently been made on a molecular basis and the following facts have been revealed. That is, capsaicin stimulates lipolysis in white adipose tissue by stimulating secretion of catecholamine from the adrenal gland and also stimulates thermogenesis in brown adipose tissue. Consequently, accumulated body fat is reduced and the serum trigliceride level is lowered.

Therefore, it would be considered advisable to take capsaicins in order to prevent or remedy obesity. However, the strong pungent-taste of capsaicin prevents its continual intake in amounts which are effective.

Accordingly, research has been made to find substances from among N-vanillyl fatty acid amides similar in chemical structure to the above-described capsaicins which have useful activities similar to the physiological activities of capsaicins without pungent-taste as strong as capsaicins. As a result, it has been confirmed that of the N-vanillyl fatty acid amides, the pungent taste peaks in those whose straight chain moiety has a carbon number of 9 and then decreases with an increase in the carbon number (with a carbon number of 11, the pungent-taste becomes weak, with a carbon number of 12, substantially non-pungent-taste is sensed, and with a carbon number of 14 or more, there is no pungent-taste) and that the catecholamine secreting effect does not change substantially with carbon numbers of 9 to 20 [Life Sciences, Vol. 54, pp. 369–374].

Discovery of capsaicin analogues with a weak pungent-taste suggests the possibility that the above-described various useful effects of capsaicin analogues can be utilized with oral administration without being obstructed by a pungent-taste.

A plant that contains abundant N-vanillyl fatty acid amides having useful bioactivities similar to those of capsaicins with substantially no pungent-taste (hereafter, referred to as "non-hot capsaicin analogues") has not been found, and, hence, application of such non-hot capsaicin analogues in the food industry would require synthesized one. The N-vanillyl fatty acid amides used in the above-described investigation of capsaicin analogues were synthesized from vanillylamine and a fatty acid chloride. However, any other production method is desirable even if the yield is somewhat poor, because acid chlorides are expensive and difficult to handle.

An object of the present invention is therefore to provide a method of producing capsaicin analogues (particularly non-hot capsaicin analogues) from a starting material other than acid chlorides.

Another object of the present invention is to enable production of capsaicin analogues (particularly non-hot capsaicin analogues) by an enzymatic reaction.

Still another object of the present invention is to provide a method of producing a non-hot capsaicin analogue from capsaicins.

Yet another object of the present invention is to provide edible fats and oils containing non-hot capsaicin analogues.

SUMMARY OF THE INVENTION

The present invention provides a method of producing a capsaicin analogue, comprising reacting a fatty acid having 12 or more carbon atoms or an ester thereof (inclusive of fats and oils) with capsaicin in the presence of lipase to produce an N-vanillyl fatty acid amide having an acyl group containing 12 or more carbon atoms.

The present invention also provides a method of producing fats and oils containing capsaicin analogues, comprising reacting edible fats and oils with capsaicin in the presence of lipase to produce N-vanillyl fatty acid amides from a portion of the edible fats and oils.

DETAILED DESCRIPTION OF THE INVENTION

The present inventors have discovered the heretofore unknown reaction described in Formula I below in which capsaicin reacts with a fatty acid or an ester thereof (inclusive of natural fats and oils) by a catalytic action of lipase to exchange acyl group, thus forming a different N-vanillyl fatty acid amide (hereafter, referred to as "Transacylation").

$$\phi\text{-CH}_2\text{NH—COR}+R_1\text{COOR}_2 \rightarrow \phi\text{-CH}_2\text{NH—COR}_1+\text{RCOOR}_2 \quad (I)$$

$\phi$: 3-CH$_3$O-4-OH—C$_6$H$_3$—

R: —CH$_2$CH$_2$CH$_2$CH$_2$CH=CHCH(CH$_3$)$_2$

R$_1$: medium or long chain aliphatic group

R$_2$: hydrogen atom or lower aliphatic group

The present invention provides a method of producing the capsaicin analogue described below and a method of producing fats and oils containing the capsaicin analogues based on the above discovery.

(1) A method of producing a capsaicin analogue, comprising reacting a fatty acid having 12 or more carbon atoms or an ester thereof (inclusive of fats and oils) with capsaicin in the presence of lipase to produce an N-vanillyl fatty acid amide having an acyl group containing 12 or more carbon atoms.

(2) A method of producing fats and oils containing capsaicin analogues, comprising reacting edible fats and oils with capsaicin in the presence of lipase to produce N-vanillyl fatty acid amides from a portion of the edible fats and oils.

The capsaicin analogues and a method of producing fats and oils containing them will be described below in detail.

The fatty acids to be reacted with capsaicin includes those which have 12 or more carbon atoms, preferably 14 to 20 carbon atoms. The fatty acids may be any one of saturated fatty acids, unsaturated fatty acids, straight chain fatty acids, branched chain fatty acids, and hydroxy fatty acids or polycarboxylic acids. More specifically, the following can be used.

Saturated straight chain fatty acids: lauric acid, myristic acid, palmitic acid, stearic acid, arachic acid, behenic acid, lignoceric acid, pentadecanoic acid, margaric acid, nonadecanoic acid, heneicosanoic acid, and tricosanoic acid.

Saturated branched chain fatty acids: isomyristic acid, isopalmitic acid, isostearic acid, isoarachic acid, and 19-methyl-eicosanoic acid.

Unsaturated fatty acids: 5-dodeoenoic acid, lauroleic acid, tsuzuic acid, physeteric acid, myristoleic acid, palmitoleic acid, petroselinic acid, oleic acid, elaidic acid, vaccenic acid, gadoleic acid, cetoleic acid, erucic acid, selacholeic acid, linoleic acid, $\alpha$-linolenic acid, $\gamma$-linolenic acid, $\alpha$-eleostearic acid, $\beta$-eleostearic acid, punicic acid, 6,9,12,15-octadecatetraenoic acid, parinaric acid, arachidonic acid, 5,8,11,14,17-eicosapentaenoic acid, 7,10,13,16,19-docosapentaenoic acid, and 4,7,10,13,16,19-docosahexaenoic acid.

Hydroxy fatty acids: $\alpha$-hydroxymyristic acid, $\alpha$-hydroxypalmitic acid, $\alpha$-hydroxystearic acid, $\alpha$-hydroxyarachic acid, 9-hydroxy-12-octadecenoic acid, ricinoleic acid, $\alpha$-hydroxybehenic acid, 18-hydroxy-trans-9, trans-11, trans-13-octadecatrienoic acid, ipurolic acid, 9,10-dihydroxystearic acid, and 12-hydroxystearic acid.

Esters of the above fatty acids may each be used as a starting material in the production method of the present invention. The number of carbons and hydroxyl groups in the alcohol moiety of the ester is not particularly limited and the alcohol moiety does not have to be a straight chain aliphatic alcohol. However, of these, those aliphatic alcohols which have up to 14 carbon atoms, particularly those which have 1 to 6 carbon atoms, are preferred and specific examples thereof include monohydric alcohols such as methyl alcohol, ethyl alcohol, n-propyl alcohol, isopropyl alcohol, n-butyl alcohol, isobutyl alcohol, and n-hexyl alcohol and polyhydric alcohols such as glycerol.

Fatty acid esters whose alcohol moiety is glycerol, i.e., glycerides, may be any one of monoesters, diesters and triesters, and mixture thereof. Hence, glycerol esters may be natural fats and oils derived from animals and plants. Actually, for safety reasons, when the products are used in the food industry, natural edible fats and oils are most preferred as a starting material for the production method of the present invention.

Most of the fatty acids which constitute triglycerides of fats and oils used for food contain 12 or more carbon atoms and, hence, the capsaicin analogues produced when fats and oils are reacted with capsaicin in fact include only non-hot capsaicin analogues.

Specific examples of available fats and oils include linseed oil, olive oil, cacao butter, tsubaki oil, rape seed oil, corn oil, sesame oil, safflower oil, perilla seed oil, wheat germ oil, palm oil, palm kernel oil, castor oil, coconut oil, peanut oil, sunflower oil, cotton seed oil, rice bran oil, soybean oil, Japan wax oil, sardine oil, bonito oil, herring oil, shark oil, avogado oil, evening primrose oil, etc.

Mixtures of two or more of the above-described fatty acids and fatty acid esters may be used as a reactant material.

The capsaicin which is reacted with a fatty acid or ester thereof, may be a commercially available one or a capsaicin-containing extract obtained from a plant containing capsaicin, such as red pepper.

To extract capsaicin from red pepper, lower alcohols, e.g., methanol, ethanol, etc., polyhydric alcohols, e.g., 1,3-butylene glycol, glycerol, etc., and hydrocarbons, e.g., hexane, etc. may be used as an extraction solvent.

It is not necessary that a particular lipase be used as a catalyst, and lipases commercially available as an enzyme for hydrolyzing glycerides or a composite enzyme preparation containing a lipase as a major component may be used. Usually, commercially available lipases are those produced from a culture solution of a microorganism capable of producing a lipase. The activity of catalyzing transacylation is independent of the type of the microorganism used in the production.

Needless to say, lipases may be used in the form of an immobilized enzyme. Alternatively, microorganism cells capable of extracellular lipase production, a culture solution thereof or a crude enzyme liquor obtained from the culture solution may be used in the present invention.

Microorganisms from which the lipase used in the present invention may be derived include, for example, the following.

Microorganisms belonging to the genus Mucor: *Mucor miehei*, and *Mucor javanicus*.

Microorganisms belonging to the genus Aspergillus: *Aspergillus niger*.

Microorganisms belonging to the genus Rhizopus: *Rhizopus delemar*, and *Rhizopus niveus*.

Microorganisms belonging to the genus Geotrichum: *Geotrichum candidum*.

Microorganisms belonging to the genus Penicillium: *Penicillium cyclopium*, and *Penicillium roquefolti*.

Microorganisms belonging to the genus Phycomyces: *Phycomyces nitens*.

Microorganisms belonging to the genus Humicola: *Humicola lanuginosa*.

Microorganisms belonging to the genus Chromobacterium: *Chromobacterium viscosum*.

Microorganisms belonging to the genus Arthrobacter: *Arthrobacter ureafaciens*.

Microorganisms belonging to the genus Pseudomonas: *Pseudomonas mephitica, Pseudomonas cepacia*, and *Pseudomonas fluorescens*.

Yeasts belonging to the genus Candida: *Candida cylindracea, Candida rugosa, Candida lipolytica*, and *Candida antarctica*.

The reaction is usually carried out in a hydrophobic organic solvent which does not inactivate lipases (e.g., hexane). However, it is carried out without solvents, if possible.

The transacylation of capsaicin by a lipase is an equilibrium reaction. Hence, in order to increase the rate of conversion of capsaicin, which is expensive, it is advantageous that a fatty acid or an ester thereof be present in the reaction system in a much greater amount than the stoichiometric amount. Usually, about 3 times or more, preferably about 30 to 1,000 times or more, by equivalent of a fatty acid or an ester thereof may be present.

Substrates and/or enzymes may be added continuously (or intermittently) to the reaction system in order to increase productivity.

Reaction conditions may be selected to optimal conditions for the lipase to be used. The reaction temperature may usually be about 5 to 95° C., preferably about 40 to 80° C.

After completion of the reaction, collection of the target product from the reaction mixture may be carried out by any means such as column chromatography.

In cases where edible fats and oils are reacted with capsaicin in order to produce fats and oils containing non-pungent capsaicin analogues, the reaction mixture is left to stand or centrifuged to separate a oil phase, then, if desired, the oil phase is subjected to treatment such as column chromatography for separation of unreacted capsaicin, washing, dehydration, deodorizing, decoloring, solvent extraction, drying, and the like before it is supplied for use.

The non-pungent capsaicin analogues or fats and oils containing the same according to the present invention may be used as a starting material for producing functional foods having anti-obesity effects, health care foods, and the like.

EXAMPLES

Methods of the present invention are illustrated with reference to the following examples, but the invention is not intended to be limited only thereto.

In the examples, the following lipases were used.

Lipase PS: manufactured by Amano Pharmaceutical Co., Ltd., derived from *Pseudomonas cepacia*.

Lipase PS-C: manufactured by Amano Pharmaceutical Co., Ltd., an immobilized enzyme of lipase PS.

Lipase AK: manufactured by Amano Pharmaceutical Co., Ltd., derived from *Pseudomonas fluorescens*.

Lipase D: manufactured by Amano Pharmaceutical Co., Ltd., derived from *Rhizopus delemar*.

Lipase F: manufactured by Amano Pharmaceutical Co., Ltd., derived from *Rhizopus niveus*.

Lipase M: manufactured by Amano Pharmaceutical Co., Ltd., derived from *Mucor javanicus*.

Lipase AY: manufactured by Amano Pharmaceutical Co., Ltd., derived from *Candida rugosa*.

Novozyme 435: manufactured by Novo Nordisk, an immobilized enzyme derived from *Candida antarctica*.

Lipase QL: manufactured by Meito Sangyo Co., Ltd., derived from *Alcaligenes sp*.

Lipase OF: manufactured by Meito Sangyo Co., Ltd., derived from *Candida cylindracea*.

The amount of N-vanillyl fatty acid amide produced by the enzymatic reaction was determined by high performance liquid chromatography under the following conditions.

Column: Wakosil 5C18 AR, 4.6×150 mm

Carrier: 100% methanol

Flow rate: 0.5 ml/min

Detection: Fluorescence detection, Ex 280 nm, Em 320 nm.

Example 1

To a solution of 9.15 mg (0.03 mmol) of capsaicin in 5,000µl of n-hexane were added 200 mg of Novozyme 435 and 834µl (3 mmol) of methyl myristrate, and the mixture was allowed to react at 70° C. for 144 hours with stirring. Thereafter, the reaction mixture was analyzed by high performance liquid chromatography to determine the amount of N-vanillylmyristamide produced. Reaction yield based on the amount of capsaicin used was 77.9%.

Example 2

To a solution of 9.15 mg (0.03 mmol) of capsaicin in 5,000µl of n-hexane were added 200 mg of Novozyme 435 and 968µl (1 mmol) of triolein, and the mixture was allowed to react at 70° C. for a predetermined time with stirring. Thereafter, the reaction mixture was analyzed by high performance liquid chromatography to determine the amount of N-vanillyloleamide produced. The reaction was carried out for various reaction times and reaction yields based on the amount of capsaicin used were determined Table 1 shows the results obtained.

TABLE 1

| Reaction Time (hour) | Yield (%) |
|---|---|
| 24 | 21.1 |
| 48 | 33.9 |
| 72 | 52.6 |
| 144 | 84.2 |

Example 3

Capsaicin and triolein were allowed to react in the same manner as in Example 2 except that the lipase was replaced by another lipase and the reaction time was fixed at 144 hours. Table 2 shows the results obtained. LDPE immobilized enzyme was prepared by the following method.

Method of immobilization: 200 mg of LDPE (low density polyethylene, manufactured by Akzo Nobel Co., 350–1,000µm) was wetted with 400µl of ethanol and shaked at room temperature for 10 minutes. To this was added an enzyme solution (a solution of 12 mg of lipase in 6 ml of 50 mM phosphate buffer at pH 7.0) and the mixture was stirred at room temperature for 1 hour. Then, LDPE was collected by filtration, which was washed with distilled water and dried under reduced pressure.

TABLE 2

| Enzyme Used | Yield (%) |
|---|---|
| Lipase PS | 1.2 |
| Lipase PS-C | 4.2 |
| LDPE immobilized Lipase AK | 0.5 |
| LDPE immobilized Lipase D | 14.8 |
| LDPE immobilized Lipase F | 4.8 |
| LDPE immobilized Lipase M | 2.1 |
| LDPE immobilized Lipase AY | 0.5 |
| Lipase QL | 12.6 |
| Lipase OF | 13.9 |

Example 4

The same experiment as in Example 2 was carried out except that triolein was replaced by the same weight of an edible fats and oils and the reaction time was set at 144 hours. Table 3 shows the results obtained. Yield was expressed in terms of total capsaicin analogue yield in percentage based on the amount of capsaicin used.

TABLE 3

| Fats and oils | Yield (%) |
|---|---|
| Olive oil | 66.4 |
| Perilla seed oil | 22.5 |
| Corn oil | 72.4 |
| Safflower oil | 70.3 |
| Sardine oil | 26.9 |

Example 5

Red pepper fruit (produced in Malawi)(1,000 g) was heated in 10 liters of a mixed solvent of n-hexane: n-propanol=8:2 under reflux, and the extract solution was concentrated under reduced pressure to obtain 62 g of an oleoresin. To the total amount of the oleoresin was added 100 ml of 70% ethanol and the mixture was stirred at room temperature for 1 hour and then left to stand. The precipitate which formed was filtered out. The filtrate obtained was concentrated under reduced pressure to obtain 7 g of red pepper extract containing capsaicin.

To a solution of 1.0 g of the red pepper extract and 100 ml of olive oil dissolved in 500 ml of n-hexane was added 20 g of Novozyme 435 and the mixture was allowed to react at 80° C. with stirring. While continuing analysis of the reaction mixture by high performance liquid chromatography, N-vanillyloleamide was produced gradually and the amount of product reached 680 mg after 144 hours.

Example 6

An extract containing capsaicin was obtained from red pepper fruit in the same manner as in Example 5 and 1 g portion thereof together with 100 ml of perilla seed oil was dissolved in 500 ml of n-hexane. To the solution was added 20 g of Novozyme 435 and the mixture was stirred at 80° C. for 144 hours continuously.

Thereafter, the reaction mixture was filtered to collect a liquid phase to obtain perilla seed oil containing 50 mg of N-vanillyloleamide, 35 mg of N-vanillyllinoleamide, and 110 mg of N-vanillyllinolenamide.

Example 7

To a solution of 9.15 mg (0.03 mmol) of capsaicin dissolved in 5,000 μl of hexane were added 200 mg of Lipase OF and 684μl (3 mmol) of myristic acid and the mixture was allowed to react at 70° C. for a predetermined time with stirring. Thereafter, the reaction mixture was analyzed by high performance liquid chromatography and the amount of N-vanillylmyristamide produced was determined.

The above-described reaction was carried out by setting the reaction time at 44 hours or 144 hours and reaction yields based on the amount of the capsaicin used were determined. Table 4 shows the results obtained.

TABLE 4

| Reaction Time (hours) | Yield (%) |
| --- | --- |
| 44 | 11.3 |
| 144 | 27.5 |

Example 8

To a solution of 18.3 mg (0.06 mmol) of capsaicin dissolved in 7,000 μl of n-hexane were added 500 mg of Lipase OF and 684 μl (3 mmol) of oleic acid and 0.08 ml of distilled water and the mixture was allowed to react at 80° C. for a predetermined time with stirring. Thereafter, the reaction mixture was analyzed by high performance liquid chromatography and the amount of N-vanillyloleamide produced was determined.

The above-described reaction was carried out for various reaction times and reaction yields based on the amount of the capsaicin used were determined. Table 5 shows the results obtained.

TABLE 5

| Reaction Time (hours) | Yield (%) |
| --- | --- |
| 24 | 45.8 |
| 48 | 61.3 |
| 120 | 73.7 |

As described above, according to the present invention, it is possible to produce non-pungent capsaicin analogues and other capsaicin analogues by enzymatic reactions, which facilitates utilization of non-pungent capsaicin analogues in the food industry.

What is claimed is:

1. A method of producing a capsaicin analogue, comprising reacting a fatty acid having 12 or more carbon atoms or an ester thereof with capsaicin in the presence of lipase to produce an N-vanillyl fatty acid amide having acyl group containing 12 or more carbon atoms.

2. A method according to claim 1, wherein said fatty acid is a fatty acid having 14 to 20 carbon atoms or an ester thereof.

3. A method according to claim 1, wherein said fatty acid is reacted with said capsaicin in n-hexane.

4. A method according to claim 1, wherein said lipase is derived from a microorganism selected from *Mucor miehei, Mucor javanicus, Aspergillus niger, Rhizopus delemar, Rhizopus niveus, Geotrichuim candidum, Penicillium cyclopium, Penicillium roqueforti, Phycomyces nitens, Humicola lanuginosa, Chromobacterium viscosum, Arthrobacter ureafaciens, Pseudomonas mephitica, Pseudomonas cepacia, Pseudomonas fluorescens, Candida cylindracea, Candida rugosa, Candida lipolytica*, and *Candida antarctica*.

5. A method according to claim 1, wherein about 30 to 1,000 times or more by equivalent of said fatty acid or said ester thereof is present in the reaction.

6. A method of producing fats and oils containing capsaicin analogues, comprising reacting edible fats and oils with capsaicin in the presence of lipase to produce N-vanillyl fatty acid amides from a portion of the fats and oils.

7. A method according to claim 6, wherein said fats and oils are esters of fatty acids having 14 to 20 carbon atoms.

8. A method according to claim 6, wherein said fats and oils are reacted with said capsaicin in n-hexane.

9. A method according to claim 6, wherein said lipase is derived from a microorganism selected from *Mucor miehei, Mucor javanicus, Aspergillus niger, Rhizopus delemar, Rhizopus niveus, Geotrichum candidum, Penicillium cyclopium, Penicillium roqueforti, Phycomyces nitens, Humicola lanuginosa, Chromobacterium viscosum, Arthrobacter ureafaciens, Pseudomonas mephitica, Pseudomonas cepacia, Pseudomonas fluorescens, Candida cylindracea, Candida rugosa, Candida lipolytica*, and *Candida antarctica*.

10. A method according to claim 6, wherein about 30 to 1,000 times or more by equivalent of said fats and oils is present in the reaction.

11. A method according to claim 1, wherein about 3 to 1000 times or more by equivalent of said fatty acid or said ester thereof is present.

12. A method according to claim 1, said further comprising a hydrophobic solvent which does not deactivate said lipase.

13. A method according to claim 1, wherein said reacting is carried out at a temperature of 40–80° C.

14. A method according to claim 6, wherein about 3 to 1000 times or more by equivalent of said fats or oils is present.

15. A method according to claim 6, further comprising a hydrophobic solvent which does not deactivate said lipase.

16. A method according to claim 6, wherein said reacting is carried out at a temperature of 40–80° C.

* * * * *